(12) United States Patent
Wanigatunga et al.

(10) Patent No.: US 7,378,556 B2
(45) Date of Patent: May 27, 2008

(54) PROCESS FOR MAKING THIOPHOSPHINE COMPOUNDS

(75) Inventors: Sirisoma Wanigatunga, Largo, FL (US); Aref Jallouli, Largo, FL (US); Martin Rickwood, Clarks Summit, PA (US); Yassin Yusef Turshani, Largo, FL (US)

(73) Assignee: Essilor International Compagnie Generale d'Optique, Charenton Cedex (FR)

( * ) Notice: Subject to any disclaimer, the term of this patent is extended or adjusted under 35 U.S.C. 154(b) by 0 days.

(21) Appl. No.: 11/551,439

(22) Filed: Oct. 20, 2006

(65) Prior Publication Data

US 2007/0232835 A1   Oct. 4, 2007

Related U.S. Application Data

(62) Division of application No. 10/807,742, filed on Mar. 24, 2004, now Pat. No. 7,129,321.

(60) Provisional application No. 60/457,042, filed on Mar. 24, 2003.

(51) Int. Cl.
  *C07F 9/02* (2006.01)
(52) U.S. Cl. .......................... 568/14; 568/15
(58) Field of Classification Search ............... 528/398, 528/373, 389; 568/14, 15
  See application file for complete search history.

(56) References Cited

U.S. PATENT DOCUMENTS

| | | | |
|---|---|---|---|
| 3,525,752 A | 8/1970 | D'Amico et al. | 549/22 |
| 3,652,256 A | 3/1972 | D'Amico | 71/90 |
| 4,698,448 A | 10/1987 | Ude et al. | 568/14 |
| 4,810,812 A | 3/1989 | Matsuda et al. | 558/251 |
| 4,847,419 A | 7/1989 | Weiss et al. | 568/14 |
| 5,384,379 A | 1/1995 | Bader et al. | 526/286 |
| 5,403,938 A | 4/1995 | Ohkubo et al. | 549/22 |
| 5,793,098 A | 8/1998 | Uchida | 257/665 |
| 5,945,504 A | 8/1999 | Amagi et al. | 528/373 |
| 2002/0061995 A1 | 5/2002 | Ohkuma et al. | 526/286 |

FOREIGN PATENT DOCUMENTS

| | | |
|---|---|---|
| EP | 273661 | 7/1988 |
| EP | 273710 | 7/1988 |
| EP | 329389 | 8/1989 |
| EP | 384725 | 8/1990 |
| EP | 0394495 | 10/1990 |
| EP | 761665 | 3/1997 |
| EP | 942027 | 9/1999 |
| EP | 1116735 | 7/2001 |
| EP | 1326095 | 7/2003 |
| WO | WO 02/24786 | 3/2002 |
| WO | WO 02/051911 | 7/2002 |

OTHER PUBLICATIONS

Dilworth et al., Synthesis of 2-Mercapto- and 2-Hydroxy-Substituted Diphenylphosphines for use as Dianionic Bidente Ligands and Polydentate Ligand Precursors, Phosphorous, Sulfur, and Silicon, 1996, vol. 111, p. 108.*
U.S. Appl. No. 11/551,409, filed Oct. 20, 2006, Wanigatunga et al.
Barbero et al., "Convenient procedure for converting 1,3-dithiolane-2-thiones into 1,3-dithiolan-2-ones," *J. Chem. Soc.*, Perkin Trans 1, 3:289-294, 1996.
Coffen, "Transesterification of orthothiocarbonates (1)," *J. Hetrocycl. Chem.*, 7:201, 1970.
Endo and Tanaka, "A new class of polymerizable sulfer heterocycles. Cationic ring-opening polymerization of spiro tetrathioorthocarbonate," *Macromolecules*, 21:2314, 1988.
Hanyu, "Silver halide photgraphic material containing phosphine chalcogenide as sensitizer," Konica Co., Japan, Chem. Abstract 128:41551, 1997.

* cited by examiner

*Primary Examiner*—Yvonne (Bonnie) Eyler
*Assistant Examiner*—Chukwuma O. Nwaonicha
(74) *Attorney, Agent, or Firm*—Fulbright & Jaworski L.L.P.

(57) ABSTRACT

Disclosed is a process for making a thiophosphine compound of formula (I):

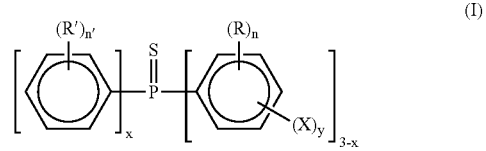

wherein X represents SH or

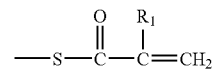

with $R_1$ being H or $-CH_3$, R and R' represent, independently from each other, an alkyl radical, an alkoxy radical, an aryl radical or a phenyl radical which may be substituted with one or more alkyl and/or alkoxy groups, n is an integer from 0 to 4, n' is an integer from 0 to 5, x is an integer from 0 to 2, y is an integer from 1 to 5 with the proviso that y+n is an integer from 1 to 5, wherein y =1, X is in para position with regard to phosphorus and represents SH.

5 Claims, No Drawings

PROCESS FOR MAKING THIOPHOSPHINE COMPOUNDS

CROSS REFERENCE TO RELATED APPLICATIONS

This application is a Divisional Application of co-pending U.S. Application No. 10/807,742 filed Mar. 24, 2004, which claims the benefit of U.S. Provisional Application No. 60/457,042 filed Mar. 24, 2003, the contents of which are incorporated by reference in their entirety.

BACKGROUND OF THE INVENTION

The present invention relates in general to thiophosphine compounds (also named phosphine sulfide compounds) and their use for making polymerizable compositions which after polymerisation give optically transparent articles, such as ophthalmic lenses, having improved mechanical and optical properties and in particular having an improved UV cut.

The use of polymerizable compositions comprising thio-urethane monomers is well known for making ophthalmic lenses. The thus obtained ophthalmic lenses exhibit a unique combination of mechanical and optical properties.

Nevertheless, there is still a need for improved materials for making ophthalmic lenses and in particular for materials having an improved UV cut, without adversely affecting the other required mechanical and optical properties.

SUMMARY OF THE INVENTION

It has now been found that the above goal can be achieved by providing a polymerizable composition which comprises:

a) at least one first polymerizable component selected from the group consisting of monomers having at least two functional groups selected from the cyanato, isocyanato, thiocyanato, isothiocyanato, (meth)acryloyl, thio(meth)acryloyl, episulfides radicals and b) at least one second polymerizable component selected from:

i) thiophosphine monomers of formula:

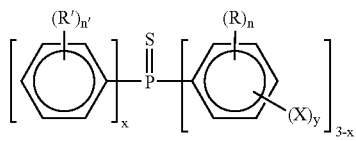

(I)

wherein X represents —SH or

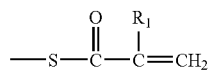

with $R_1$ being H or —$CH_3$, R and R' are, independently from each other, an alkyl radical, an alkoxy radical or a phenyl radical which may be substituted with one or more alkyl and/or alkoxy groups, n is an integer from 0 to 4, n' is an integer from 0 to 5, x is an integer from 0 to 2 and y is an integer from 1 to 5 with the proviso that y+n is an integer from 1 to 5; and ii) prepolymers resulting from the polymerization of at least one of said thiophosphine monomers of formula (I) and at least one of said first polymerizable component and preferably having a number average molecular weight ranging from 1 000 to 10 000.

The first polymerizable components of the compositions of the present invention can be monomers selected from the group consisting of polycyanate, polyisocyanate, polythiocyanate, polyisothiocyanate, poly(meth)acrylate, polythio(meth)acrylate, polyepisulfide and mixtures thereof.

The polycyanate and polythiocyanate monomers used in the present invention can be any polycyanate and polythiocyanate monomers having two or more cyanate or thiocyanate functions per molecule, preferably two or three and more preferably two.

The polyisocyanate or polyisothiocyanate monomers included in the polymerizable compositions according to the invention may be any polyisocyanate or polyisothiocyanate monomer having two or more isocyanate or isothiocyanate functions per molecule, preferably two or three isocyanate or isothiocyanate functions and more preferably two isocyanate or isothiocyanate functions.

The preferred polyisocyanate or isothiocyanate monomers are those having the formulae:

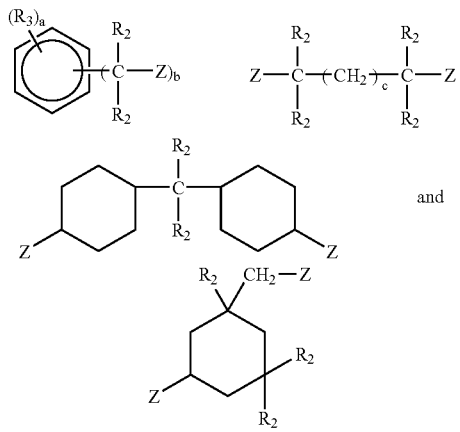

and wherein $R_2$ is independently H or a $C_1$-$C_5$ alkyl group, preferably $CH_3$ or $C_2H_5$;

$R_3$ is H, an halogen, preferably Cl or Br, or a $C_1$-$C_5$ alkyl group, preferably $CH_3$ or $C_2H_5$;

Z is —N═C═A, with A being O or S;

a is an integer ranging from 1 to 4, b is an integer ranging from 2 to 4 and a+b≦6; and c is an integer from 1 to 10, preferably 1 to 6.

Among the preferred polyisocyanate or isothiocyanate monomers there may be cited tolylene diisocyanate or diisothiocyanate, phenylene diisocyanate or diisothiocyanate, ethylphenylene diisocyanate, isopropyl phenylene diisocyanate or diisothiocyanate, dimethylphenylene diisocyanate or diisothiocyanate, diethylphenylene diisocyanate or diisothiocyanate, diisopropylphenylene diisocyanate or diisothiocyanate, trimethylbenzyl triisocyanate or triisothiocyanate, xylylene diisocyanate or diisothiocyanate, benzyl triiso(thio)cyanate, 4,4'-diphenyl methane diisocyanate or diisothiocyanate, naphtalene diisocyanate or diisothiocyanate, isophorone diisocyanate or diisothiocyanate, bis(isocyanate or diisothiocyanate methyl)cyclohexane, hexamethylene diisocyanate or diisothiocyanate and dicyclohexylmethane diisocyanate or diisothiocyanate.

The poly(meth)acrylate monomers included in the polymerizable compositions according to the invention can be any poly(meth)acrylate monomer commonly used for making ophthalmic lenses and in particular, di, tri or tetra(meth)acrylate monomers. Preferably, the poly(meth)acrylate monomers are di(meth)acrylate. Among the preferred di(meth)acrylate there may be cited alkyleneglycol di(meth)acrylates, preferably ethyleneglycol di(meth)acrylate and propyleneglycol di(meth)acrylate, polyalkyleneglycol di(meth)acrylates, preferably polyethyleneglycol di(meth)acrylates and polybutyleneglycol di(meth)acrylates, neopentylglycol di(meth)acrylate, and derivates of bisphenol-A di(meth)acrylates.

The bisphenol-A di(meth)acrylates compounds may include the compounds of the formula:

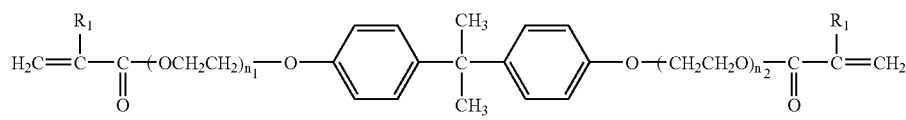

wherein $R_1$ is H or $CH_3$ and $n_1+n_2$ has a mean value in the range of 0 to 40.

Preferred compounds having the above-mentioned formula are those for which $R_1$ is $CH_3$ and $n_1+n_2=2,6$ (EBADMA), $n_1+n_2=4$ (DBADMA), $n_1+n_2=10$ (OBADMA) and $n_1+n_2=30$.

The polythio(meth)acrylate monomers included in the polymerizable compositions of the invention can be any poly(meth)acrylate monomer commonly used for making ophthalmic lenses. In particular, said polythio(meth)acrylate monomers may have the following formula:

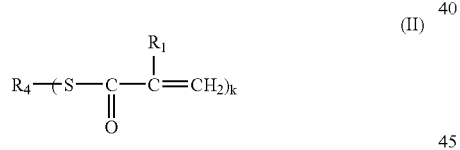

wherein:

$R_4$ is a linear or branched, polyvalent aliphatic hydrocarbon radical, or a polyvalent aromatic group, directly linked to the sulphur atom of the thio(meth)acrylate groups with an aromatic ring or by means of a linear alkyl chain, said $R_4$ radical being able to include in its chain one or more groups selected amongst —O—, —S— and carbonyl group, $R_1$ is hydrogen or —$CH_3$, and k is an integer from 2 to 6, preferably from 2 to 3.

When $R_4$ is a divalent radical, a preferred class of thio(meth)acrylate monomers includes:

a) the monomers of the formula

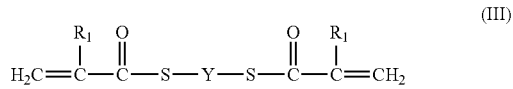

wherein Y is a linear or branched $C_2$-$C_{12}$ alkylene group, a $C_3$-$C_{12}$ cycloalkylene group, a $C_6$-$C_{14}$ arylene group or a $C_7$-$C_{26}$ alkarylene group, where the Y carbon chains can be interrupted by one or more oxygen and/or sulfur atoms and $R_1$ is hydrogen or a methyl group, b) the monomers of the formula:

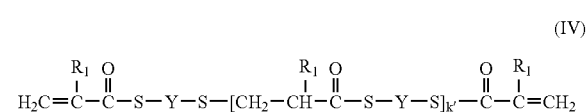

wherein $R_1$ and Y are defined as above, and k' is an integer from 1 to 10, preferably 1 to 6, and the mixtures thereof.

Preferred divalent Y radicals may include:

a) the radicals of the formulae:

—$(CH_2)_j$— where j is an integer from 2 to 8,

—$(CH_2CH_2O)_{y'}CH_2CH_2$— where y' is an integer from 1 to 4,

—$(CH_2CH_2S)_{n}CH_2CH_2$— where z is an integer from 1 to 4,

—$(CH_2)_{u'}(S(CH_2)_{v'})_{x'}S$—$(CH_2)_{w'}$ where x' is 0 or 1 and u', v', w' are integers from 2 to 6, b) the radicals of the formula

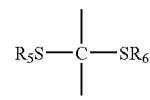

wherein $R_5$ and $R_6$ are $C_1$-$C_5$ alkyl radicals;

c) the radicals of the formula:

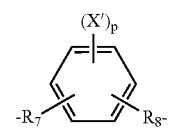

wherein $R_7$ and $R_8$ are linear or branched $C_1$-$C_5$ alkylene groups, that can include one or more —O—, —S— or carbonyl groups in their chains and X' is selected from the $C_1$-$C_5$ alkyl radicals and halogens, and p is an integer from 0 to 4;

more particularly the radicals of the formula:

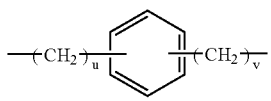

wherein u and v are integers from 1 to 4;
d) the radicals of the formula

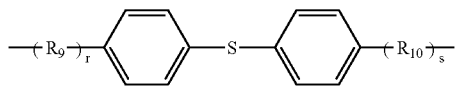

wherein $R_9$ and $R_{10}$ are linear or branched $C_1$-$C_5$ alkyl radicals, that can include in their chains one or more —O—, —S— or carbonyl groups and r and s are 0 or 1.

Divalent monomers of the formula (II) are disclosed, inter alia, in EP-A-273,661, EP-A-273,710, EP-A-384,725.

The monomers of formulae (III) and (IV) are disclosed in U.S. Pat. No. 5,384,379.

The trivalent $R_4$ radicals of the monomers of formula (II) may include $C_3$-$C_{10}$ alkyltriyl radicals that can include in their chains one or more —O—, —S— or carbonyl groups, trivalent alkylaryl radicals the alkyl chains of which can include one or more —S— or —O— groups, and trivalent aryl groups.

The trivalent $R_4$ radicals or higher valency radicals may include:

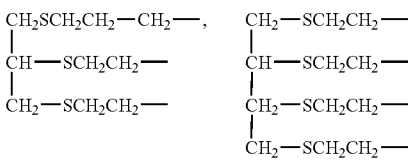

The thio(meth)acrylate monomers being recommended in the present invention include:

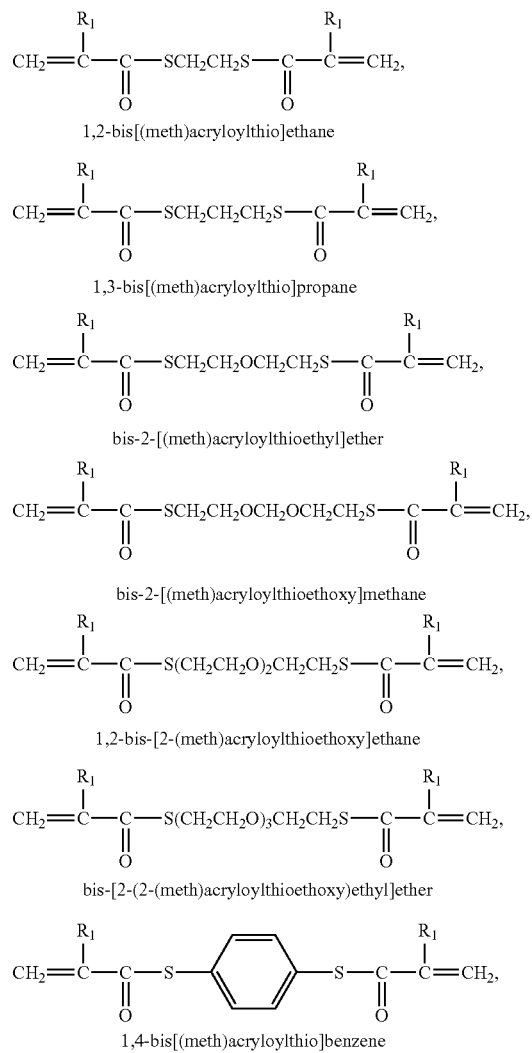

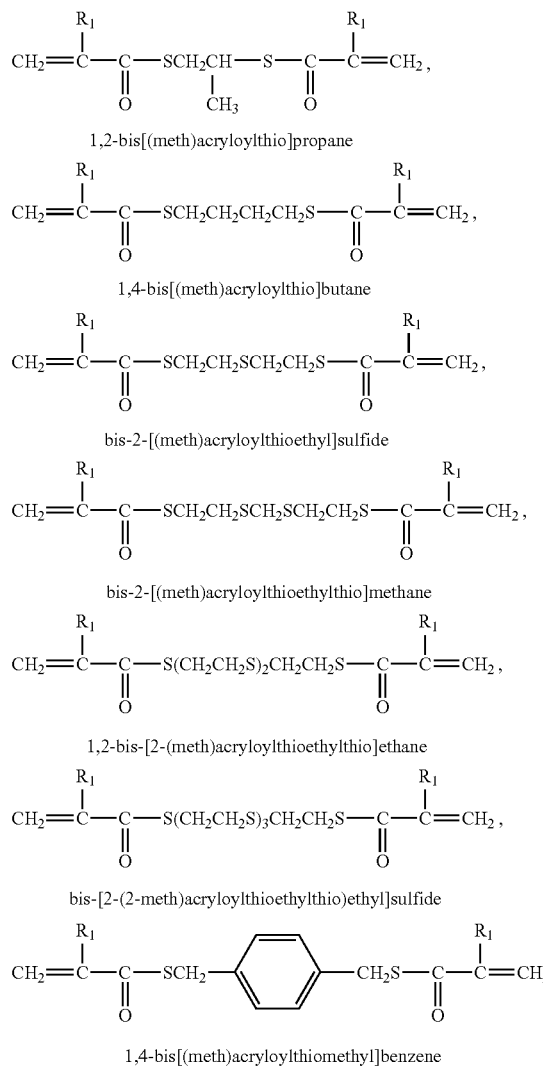

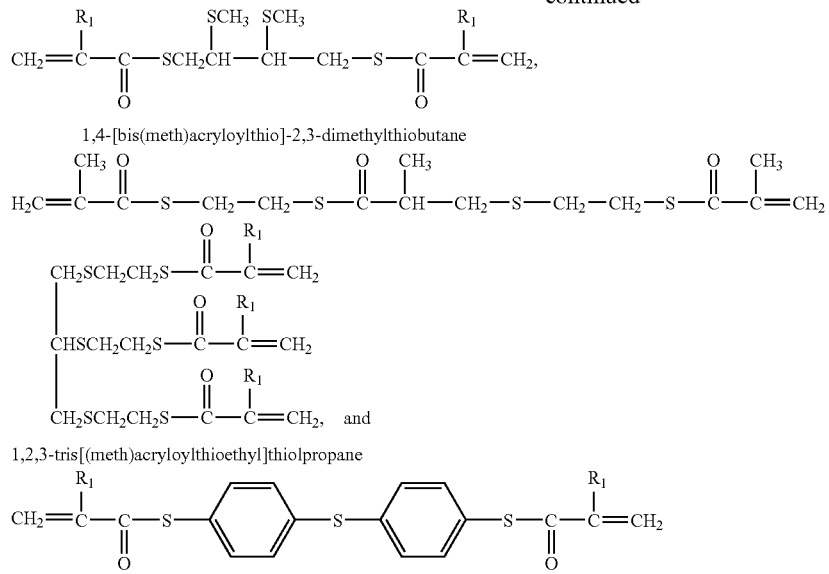

1,4-[bis(meth)acryloylthio]-2,3-dimethylthiobutane 1,2,3-tris[(meth)acryloylthioethyl]thiolpropane bis[(meth)acryloylthiophenyl]sulfide, where $R_1$ is a hydrogen atom or a methyl group.

The polyepisulfide monomers included in the polymerizable compositions according to the invention are preferably diepisulfide monomers and are disclosed, for instance, in the following patents: EP 942 027, U.S. Pat. No. 5,945,504, EP 761 665.

Preferably, the first polymerizable component or components of the composition of the present invention represent 25 to 70% by weight based on the total weight of the polymerizable components present in the composition. More preferably, said first polymerizable component or components represent 30 to 50% by weight.

Besides first polymerizable components, one other essential component of the polymerisable compositions of the present invention is the second component (b).

As previously indicated this second component can be a thiophosphine monomer of formula (I) or a mixture thereof.

Preferred thiophosphine monomers of formula I are those in which y=1.

Also preferred thiophosphine monomers of formula I are those in which n and n' are equal to zero.

Also preferably X represents —SH.

As previously mentioned R and R' may represent alkyl, alkoxy or phenyl radicals which may be substituted with one or more alkyl and/or alkoxy groups.

Typically, alkyl radicals are $C_1$-$C_6$ alkyl radicals, such as methyl, ethyl, butyl, preferably methyl, and alkoxy radicals are $C_1$-$C_6$ alkoxy radicals such as methoxy, ethoxy and propoxy radicals.

The most preferred thiophosphine monomers are:

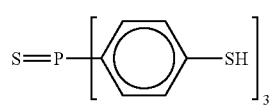

Tris(4-thiophenyl)phosphine sulphide
(TTPPS)

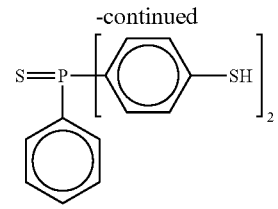

Bis(4-thiophenyl)phenyl phosphine sulfide
(BTPPS)

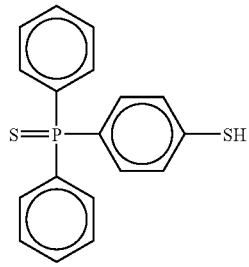

Bisphenyl-4-thiophenylphosphine sulphide
(BPTTS)

Preferably, the thiophosphine monomers represent 1 to 25%, preferably 1 to 15%, by weight based on the total weight of the polymerizable components present in the composition. More preferably, the thiophosphine monomers represent 1 to 10% by weight.

The second polymerizable components of the compositions of the invention can also be prepolymers resulting from the polymerization of at least one thiophosphine monomer of formula (I) and at least one of said first polymerizable component.

Preferably, said first polymerizable components used for making said prepolymers are selected from the group consisting of dicyanate, dithiocyanate, diisocyanate, diisothiocyanate, di(meth)acrylate, dithio(meth)acrylate and diepisulfide monomers.

Preferably, prepolymers of the present invention have a number average molecular weight. Mn ranging from 1 000 to 10 000.

Preferably, said prepolymers represent up to 40% by weight based on the total weight of the polymerizable components present in the composition, preferably less than 30% by weight.

In addition to said first and second polymerizable components, the compositions of the invention may comprise one or more additional polymerizable monomers different from first and second components. Such additional monomers may be selected from polythiols and polyvinyl monomers.

Preferably, at least one additional monomer is selected from polythiols.

The polythiol monomers included in the polymerizable compositions according to the invention are well known in the art and can be represented with the formula R"(SH)$_{n''}$, wherein n" is an integer of 2 or more, preferably from 2 to 5, and R" is an aliphatic, aromatic or heterocyclic radical.

The polythiol monomers are preferably dithiol, trithiol or tetrathiol monomers.

These polythiol compounds are well known in the art and are disclosed, among others, in EP 394,495.

The dithiols useful in the present invention may include 9,10-anthracenedimethanethiol, 1,11-undecanedithiol, 4-ethyl-benzene-1,3-dithiol, 1,2-ethanedithiol, 1,8-octanedithiol, 1,18-octadecanedithiol, 2,5-dichlorobenzene-1,3-dithiol, 1,3-(4-chlorophenyl)propane-2,2-dithiol, 1,1-cyclohexanedithiol, 1,2-cyclohexanedithiol, 1,4-cyclohexanedithiol, 1,1-cycloheptanedithiol, 1,1-cyclopentanedithiol, 4,8-dithioundecane-1,11'-dithiol, dithiopentaerythritol, dithiothreitol, 1,3-diphenylpropane-2,2-dithiol, 1,3-dihydroxy-2-propyl-2',3'-dimercaptopropylether, 2,3-dihydroxypropyl-2',3'-dimercaptopropylether, 2,6-dimethyloctane-2,6-dithiol, 2,6-dimethyloctane-3,7-dithiol, 2,4-dimethylbenzene-1,3-dithiol, 4,5-dimethylbenzene-1,3-dithiol, 3,3-dimethylbutane-2,2-dithiol, 2,2-dimethylpropane-1,3-dithiol, 1,3-di(4-methoxy-phenyl)propane-2,2-dithiol, 3,4-dimethoxybutane-1,2-dithiol, 10,11-dimercaptoundecanoic acid, 6,8-dimercapto-octanoic acid, 2,5-dimercapto-1,3,4-thiadiazole, 2,2'-dimercapto-biphenyl, 4,4'-dimercaptobiphenyl, 4,4'-dimercaptobibenzyl, 3,4-dimercaptobutanol, 3,4-dimercaptobutylacetate, 2,3-dimercapto-1-propanol, 1,2-dimercapto-1,3-butanediol, 2,3-dimercaptopropionic acid, 1,2-dimercaptopropylmethylether, 2,3-dimercaptopropyl-2',3'-dimethoxypropylether, 3,4-thiophenedithiol, 1,10-decanedithiol, 1,12-dodecanedithiol, 3,5,5-trimethyl-hexane-1,1-dithiol, 2,5-toluenedithiol, 3,4-toluenedithiol, 1,4-naphthalenedithiol, 1,5-naphthalenedithiol, 2,6-naphthalenedithiol, 1,9-nonanedithiol, norbornene-2,3-dithiol, bis(2-mercaptoisopropyl)ether, bis(11-mercaptoundecyl)sulfide, bis(2-mercaptoethyl)ether, bis(2-mercaptoethyl)sulfide, bis(18-mercatooctadecyl)sulfide, bis(8-mercaptooctyl)sulfide, bis(12-mercaptodecyl)sulfide, bis(9-mercaptononyl)sulfide, bis(4-mercaptobutyl)sulfide, bis(3-mercaptopropyl)ether, bis(3-mercaptopropyl)sulfide, bis(6-mercaptohexyl)sulfide, bis(7-mercaptoheptyl)sulfide, bis(5-mercaptopentyl)sulfide, 2,2'-bis(mercaptomethyl)acetic acid, 1,1-bis(mercaptomethyl)cyclohexane, bis(mercaptomethyl)durene, phenylmethane-1,1-dithiol, 1,2-butanedithiol, 1,4-butanedithiol, 2,3-butanedithiol, 2,2-butanedithiol, 1,2-propanedithiol, 1,3-propanedithiol, 2,2-propanedithiol, 1,2-hexanedithiol, 1,6-hexanedithiol, 2,5-hexanedithiol, 1,7-heptanedithiol, 2,6-heptanedithiol, 1,5-pentanedithiol, 2,4-pentanedithiol, 3,3-pentanedithiol, 7,8-heptadecanedithiol, 1,2-benzenedithiol, 1,3-benzenedithiol, 1,4-benzenedithiol, 2-methylcyclohexane-1,1-dithiol, 2-methylbutane-2,3-dithiol, ethyleneglycol dithioglycolate, ethylene glycol bis(3-mercaptopropionate). The trithiols may include 1,2,3-propanetrithiol, 1,2,4-butanetrithiol, trimethylolpropanetrithiol glycolate, trimethylolpropane tris(3-mercaptopropionate), pentaerythritol trithioglycolate, pentaerythritol tris(3-mercaptopropionate), 1,3,5-benzenetrithiol and 2,4,6-mesitylenetrithiol.

The polythiols useful in the compositions of the present invention may further include neopentane tetrathiol, 2,2'-bis-(mercaptomethyl)-1,3-propanedithiol, pentaerythritol tetrakis(3-mercaptopropionate), pentaerythritol tetrakis(thioglycolate), 1,3,5-benzenetrithiol, 2,4,6-toluenetrithiol, 2,4,6-methylenetrithiol and the polythiols of the following formulae:

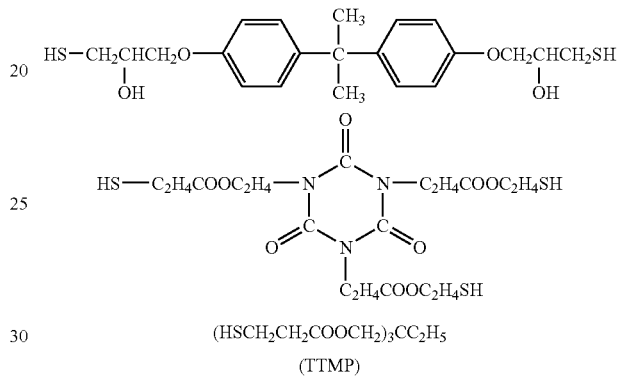

(HSCH$_2$CH$_2$COOCH$_2$)$_3$CC$_2$H$_5$
(TTMP)

and 4-mercaptomethyl-3,6-dithia-1,8-octanedithiol.

The preferred polythiols according to the present invention are ethyleneglycol bis(thioglycolate), trimethylolpropane tris(3-mercaptopropionate), pentaerythritol tetrakis thiopropionate (PETP), 4-mercaptomethyl-3,6-dithia-1,8-octanedithiol (MDO), bis(2-mercaptoethyl)sulfide (DMDS) and pentaerythritol tetrakis thioglycolate (PETG).

Preferably, said additional polymerizable monomers represent 25 to 50% by weight based on the total weight of polymerizable monomers present in the composition.

The polymerizable compositions according to the invention may also include conventionally used additives in polymerizable compositions for moulding optical items, more particularly spectacle glasses, in the conventional proportions, namely inhibitors, dyes, UV absorbers, perfumes, deodorants, antioxidants and anti-yellowing additives.

More particularly, the anti-yellowing agents such as those disclosed in the U.S. Pat. Nos. 5,442,022, 5,545,828, 5,702,825 and 5,741,831 may be used.

The preferred anti-yellowing agent is 3-methyl 2-butene 1-ol (MBOL).

Triphenylphosphine (TPP) and Irganox® 1010 (pentaerythritol-tetrakis[3(3,5-di-tert.-butyl-4-hydroxyphenyl) propionate] (CG 1010) may be mentioned as preferred examples of antioxidant agents.

Perfumes make it possible to hide the smell from the compositions, more particularly in surfacing operations.

The polymerizable compositions according to the invention may be thermal and/or UV curable compositions. Therefore, the compositions generally include at least one polymerization initiator selected from photoinitiators, thermal initiators and mixtures thereof, preferably in a proportion of 0.001% to 5% by weight based on the total weight of the polymerizable monomers present in the composition.

The photoinitiators useful in the polymerizable compositions according to the invention may include more particularly 2,4,6-trimethylbenzoyidiphenylphosphine oxide (TPO), 1-hydroxycyclo-hexylphenylketone, 2,2-dimethoxy-1,2-diphenylethane 1-one, alkylbenzoylethers, the commercially available photoinitiator from Ciba-Geigy Corporation under the tradename CGI 1700, which is a 25/75 mixture of a compound of the formula:

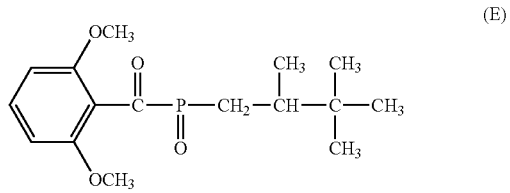

(E)

and a compound of the formula:

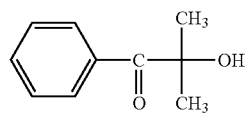

and the CGI 1850 photoinitiator commercially available from Ciba Geigy Corporation, which is a 50/50 mixture (by weight) of compound E and Irgacure® 184 of the formula:

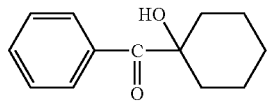

Another preferred photoinitiator is CGI 819 from Ciba Geigy Corporation of the formula:

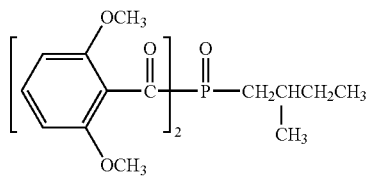

Other photoinitiators of the same type may also be used, such as that of the formula:

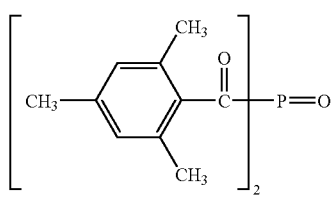

The thermal polymerization initiators are compounds which are well known in the art and may include peroxides, such as benzoyl peroxide, cyclohexyl peroxydicarbonate, isopropyl peroxydicarbonate and tert-butylperoxy(2-ethyl hexanoate).

The polymerization can be effected with or without a polymerization catalyst. Catalyst may be any known catalyst for the polymerization of the monomer.

Among the useful catalysts, there may be cited dimethyltindichloride, dibutyltindichloride and dibutyltindilaurate. Cocatalysts or promoters such as N,N-dimethylcyclohexylamine and 1,4-diazabicyclo-[2,2,2]-octane (DABCO) could also be used with the catalyst to enhance its activity.

Another object of the invention is to provide an article obtained by thermal and/or UV cure of a polymerizable composition as described above. Said article may be an ophthalmic lens.

Another object of the invention is to provide a process for making said thiophosphine compound of formula (I).

The process will be described in detail for a thiophosphine compound of formula (I) wherein y=1, X being in para position with regard to phosphorus.

When X represents —SH, said process may comprises the following steps:

a) reacting in the presence of a catalyst a component A of formula:

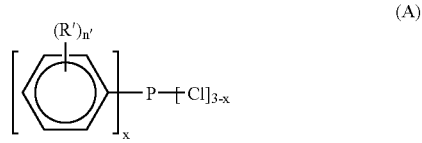

(A)

in which R', n' and x are as defined above with a component B of formula:

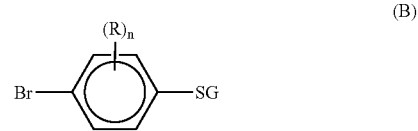

(B)

in which R and n are as previously defined and G is a blocking radical of the SH function, the molar ratio of components A to B being:
1/3 when x=0
1/2 when x=1, and
1/1 when x=2;

b) isolating from step a) a first intermediate compound C of formula:

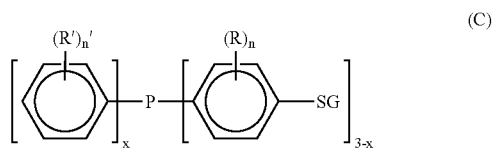

(C)

c) reacting compound C with elemental sulfur;
d) isolating from step c) an intermediate compound D of formula:

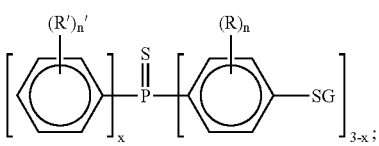

e) reacting intermediate compound D with an alkaline thiolate in a solvent under reflux; and f) isolating from step e) a thiophosphine monomer of formula (I).

G may be any known radical used as a blocking radical of the SH function.

Preferably G is $CH_3$.

Preferably the thiolate is sodium 2-methyl-2-propane thiolate.

Preferably the catalyst of step a) is n-butyl lithium.

Another process for making a thiophosphine monomer wherein y=1, X is in para position with regard to phosphorus and represents —SH, and wherein x=0 may comprises the following steps:

a) reacting in the presence of a catalyst a component A' of formula:

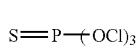

with a component B of formula:

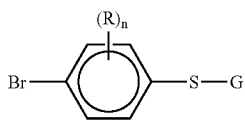

in a molar ratio A'/B equal to 1/3, where R, n and G are as defined above;

b) isolating from step a) an intermediate compound of formula D':

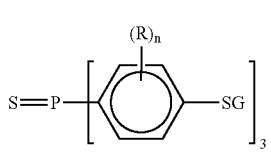

c) reacting intermediate compound D' with an alkaline thiolate in a solvent under reflux; and d) isolating from step c) a thiophosphine monomer of formula:

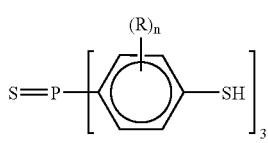

where R and n are as defined above.

G may be any known radical used as a blocking radical of the SH function.

Preferably, G is $CH_3$.

Preferably, the thiolate is sodium 2-methyl-2-propane thiolate.

Preferably, the catalyst is n-butyl lithium.

The present invention will now be described more in details in the following examples.

DETAILED DESCRIPTION

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of tris(4-thiophenyl)phosphine sulphide

Tris(4-thiophenyl)phosphine sulphide is prepared using the process according to the invention.

a) Preparation of tris(4-thioanisyl)phosphine

A cooled solution of 4-bromothioanisole (190.8 g; 0.94 mol) and anhydrous tetrahydrofuran (750 ml) under nitrogen was treated dropwise with 2.5 M n-Butyllithium (375 ml; 0.94 mol) in tetrahydrofuran. The cooled mixture was then treated dropwise with a solution of phosphorus trichloride (39.0 g; 0.28 mol) and anhydrous tetrahydrofuran (100 ml). The resulting mixture was allowed to warm to room temperature and left to stir for 52 hours. The reaction was quenched with water (500 ml) and extracted with diethyl ether. The combined extracts were dried with magnesium sulphate, filtered and evaporated to dryness to give a pasty yellow solid. Trituration with ethanol yielded tris(4-thioanisyl)phosphine (V) as a white solid (33.8 g; 30% yield).

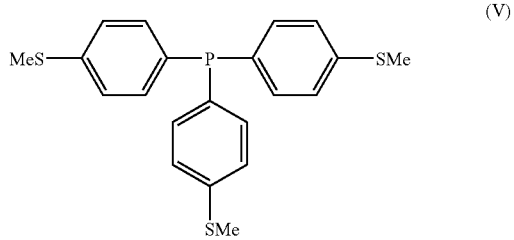

b) Preparation of tris(4-thioanisyl)phosphine sulphide

A stirred solution of tris(4-thioanisyl)phosphine (30.2 g; 0.075 mol), elemental sulphur (2.4 g; 0.075 mol) and anhydrous toluene (850 ml) under nitrogen was heated at reflux for 20 hours. The reaction mixture was evaporated to dryness and the resulting solid triturated with ethanol to give tris(4-thioanisyl)phosphine sulphide (VI) as a white solid (26.1 g; 80% yield).

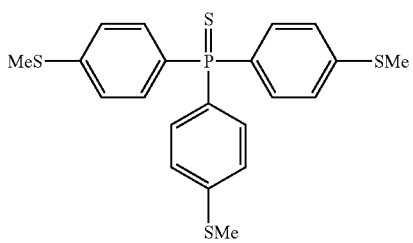

(VI)

Compound of formula (VI) can also be obtained by the following process.

A cooled solution of 4-bromothioanisole (10.0 g; 0.049 mol) and anhydrous tetrahydrofuran (50 ml) under nitrogen was treated dropwise with 2.5 M n-Butyllithium (20 ml; 0.05 mol) in tetrahydrofuran. The cooled mixture was then treated dropwise with a solution of thiophosphoryl chloride (2.78 g; 0.016 mol) and anhydrous tetrahydrofuran (5 ml). The resulting mixture was allowed to warm to room temperature and left to stir for 20 hours. The reaction was quenched with water and extracted with diethyl ether. The combined extracts were dried with magnesium sulphate, filtered and evaporated to dryness to give tris(4-thioanisyl) phosphine sulphide as a pale yellow solid (1.64 g; 23% yield).

c) Preparation of tris(4-thiophenyl)phosphine sulphide

A stirred solution of tris(4-thioanisyl)phosphine sulphide (10.0 g; 0.023 mol), sodium 2-methyl-2-propanethiolate (15.56 g; 0.139 mol) and anhydrous DMF (150 ml) under nitrogen was heated under reflux for 24 hours. The reaction mixture was cooled to 0° C. and treated with 3M HCl (50 ml) to precipitate a white solid. The solid was dissolved in dichloromethane and washed several times with water. The dichloromethane solution was dried, filtered and evaporated to afford tris(4-thiophenyl)phosphine sulphide (VII) as a white solid (5.87 g; 65% yield).

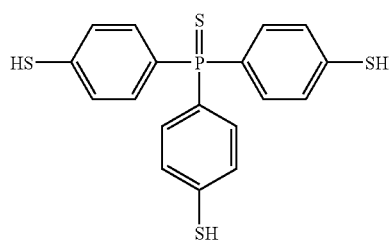

(VII)

Example 2

Synthesis of bis(4-thiophenyl)phenylphosphine sulphide

Bis(4-thiophenyl)phenylphosphine sulphide is prepared using the process according to the invention.

a) Preparation of bis(4-thioanisyl)phenyl Phosphine

A cooled solution of 4-bromothioanisole (160.0 g; 0.784 mol) and anhydrous tetrahydrofuran (500 ml) under nitrogen was treated dropwise with 2.5 M n-Butyllithium (313.6 ml; 0.784 mol) in tetrahydrofuran. The cooled mixture was treated dropwise with a solution of dichlorophenylphosphine (53.28 ml; 0.392 mol) and anhydrous tetrahydrofuran (100 ml). The resulting mixture was allowed to warm to room temperature and left to stir for 48 hours. The turbid reaction mixture was quenched with water and extracted several times with diethyl ether. The combined extracts were dried with magnesium sulphate, filtered and evaporated to dryness to give a pasty yellow solid. Trituration with ethanol yielded bis(4-thioanisyl)phenyl phosphine (VIII) as a white solid (89.3 g; 63% yield).

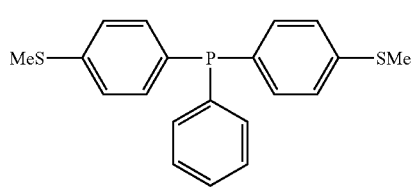

(VIII)

b) Preparation of bis(4-thioanisyl)phenylphosphine sulphide

A stirred solution of bis(4-thioanisyl)phenylphosphine (25.0 g; 0.071 mol), elemental sulphur (2.3 g; 0.070 mol) and anhydrous toluene (500 ml) under nitrogen was heated at reflux for 20 hours. The reaction mixture was evaporated to dryness and the resulting solid triturated with ethanol to give bis(4-thioanisyl)phenylphosphine sulphide (IX) as a white solid (17.2 g; 71% yield).

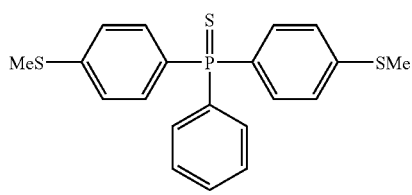

(IX)

c) Preparation of bis(4-thiophenyl)phenylphosphine sulphide

A stirred solution of bis(4-thioanisyl)phenylphosphine sulphide (4.28 g; 0.011 mol), sodium 2-methyl-2-propanethiolate (4.97 g; 0.044 mol) and anhydrous DMF (50 ml) under nitrogen was heated under reflux for 21 hours. The reaction mixture was cooled to 0° C. and treated with 3M HCl to precipitate a white solid. Trituration with diethyl ether gave bis(4-thiophenyl)phenylphosphine sulphide (X) as a white solid (3.14 g; 79% yield).

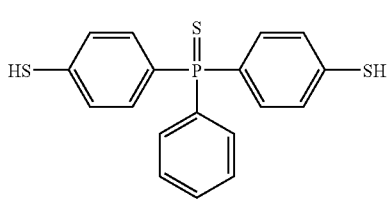

(X)

Example 3

Synthesis of bisphenyl-4-thiophenylphosphine sulphide

Bisphenyl-4-thiophenylphosphine sulphide is prepared using the process according to the invention.

a) Preparation of bisphenyl-4-thioanisylphosphine

A cooled solution of 4-bromothioanisole (10.2 g; 0.05 mol) and anhydrous tetrahydrofuran (50 ml) under nitrogen was treated dropwise with 2.5 M n-Butyllithium (19.92 ml; 0.05 mol) in tetrahydrofuran. The cooled mixture was then treated dropwise with a solution of chlorodiphenylphospine (10.0 g; 0.045 mol) and anhydrous tetrahydrofuran (10 ml). The resulting mixture was allowed to warm to room temperature and left to stir for 55 hours. The reaction was quenched with water (500 ml) and extracted with diethyl ether. The combined extracts were dried with magnesium sulphate, filtered and evaporated to dryness to give a yellow solid. Recrystallisation from butanol afforded bisphenyl-4-thioanisylphosphine (XI) as a white solid (3.26 g; 23%).

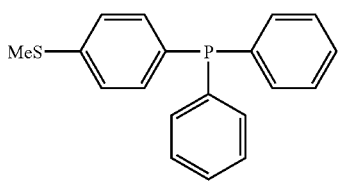

(XI)

b) Preparation of bisphenyl-4-thioanisylphosphine sulphide

A stirred solution of bisphenyl-4-thioanisylphosphine (1.84 g; 0.006 mol), elemental sulphur (0.20 g; 0.006 mol) and anhydrous toluene (35 ml) under nitrogen was heated at reflux for 6 hours. The reaction mixture was evaporated to dryness and the resulting pale yellow solid triturated with ethanol to bisphenyl-4-thioanisylphosphine sulphide (XII) as a white solid (2.00 g; 98% yield).

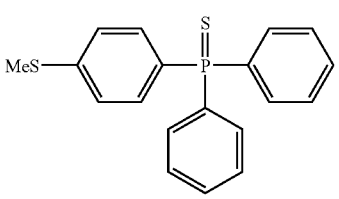

(XII)

c) Preparation of bisphenyl-4-thiophenylphosphine sulphide

A stirred solution of bisphenyl-4-thioanisylphosphine sulphide (1.73 g; 0.005 mol), sodium 2-methyl-2-propanethiolate (1.14 g; 0.010 mol) and anhydrous DMF (50 ml) under nitrogen was heated under reflux for 20 hours. The reaction mixture was cooled to 0° C. and acidified to pH 1 with 3M HCl and extracted with dichloromethane and the extract washed with a further quantity of 3M HCl (50 ml). The dichloromethane extract was dried, filtered and evaporated to give a wet brown solid which was triturated with ethanol to give crude tris(4-thiophenyl)phosphine sulphide as a yellow solid (1.10 g; 66% yield). The crude solid was chromatographed over silica ($CHCl_3$) and the resulting material recrystallised from ethanol to give tris(4-thiophenyl)phosphine sulphide (formula XIII) as a yellow solid.

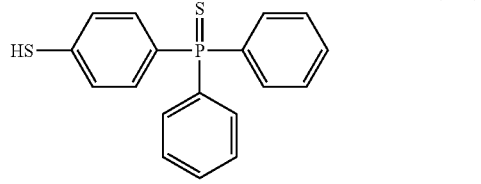

(XIII)

Examples 4, 5 and 6

Articles Obtained from Polymerizable Compositions

1. Preparation of the Polymerizable Compositions

Two compositions of polymerizable monomers according to the invention and one comparative composition have been formulated by mixing the monomers indicated in table I hereunder.

TABLE I

|  | Example 4 (comparative) | Example 5 | Example 6 |
|---|---|---|---|
| TTPPS % (1) | 0 | 4 | 8 |
| MonY | 12.135 | 11.444 | 11.867 |
| TTPPS |  | 1.044 | 2.337 |
| MonX | 13.415 | 13.43 | 14.792 |
| Catalyst solution (1% in monY) | 0.209 | 0.224 | 0.249 |

(1) % by weight with regard to total weight TTPPS + MonY + MonX

The quantities of MonY, TTPPS, MonX and catalyst solution are given in parts by weight.

TTPPS: (4-thiophenyl)phosphine sulphide

MonY: 4-mercaptomethyl-3,6-dithia-1,8-octanedithiol

MonX: dimethylphenylene diisocyanate

Catalyst: dibutyl tin dilaurate

The catalyst solution is made at room temperature. TTPPS is dissolved in Mon Y. After about 30 minutes, this becomes an emulsion. Mon X is then added. The emulsion clears up in 5 to 10 minutes.

The solution obtained is then allowed to degas. The more TTPPS is present, the more degassing is needed.

2) Casting Process

The compositions prepared as above mentioned are cast into moulds made of two mineral glass mould parts.

The composition is cured by heating.

The features of the resulting substrates are indicated in Table II.

TABLE II

|  | Example 4 (comparative) | Example 5 | Example 6 |
|---|---|---|---|
| % TTPPS | 0.0 | 4.0 | 8.0 |
| Center Thickness (mm) | 2.02 | 1.95 | 2.28 |
| Barcol | 92.2 | 92.8 | 92.6 |
| Microhardness ($N/mm^2$) | 223.3 | 223.6 | 228.7 |
| 0.5% T UV Cut (nm) | 293 | 344 | 356 |

TABLE II-continued

|  | Example 4 (comparative) | Example 5 | Example 6 |
|---|---|---|---|
| 1.0% T UV Cut (nm) | 295 | 347 | 358 |
| Tg (° C.) (DSC) | 90.3 | 94.0 | 99.7 |
| max tg(δ) (° C.) (DMA) | 102.2 | 100.8 | 110.1 |
| E' × $10^{-9}$ at 25° C. (Pa) | 3.06 | 3.48 | 3.02 |
| E' × $10^{-9}$ at 100° C. (Pa) | 0.10 | 0.18 | 0.59 |
| $n_d$ | 1.66017 | 1.66446 | 1.66756 |
| $n_e$ | 1.66509 | 1.66964 | 1.67296 |
| $v_d$ | 32 | 31 | 30 |
| $v_e$ | 32 | 31 | 29 |

Barcol test: The Barcol hardness of the lens is measured by using a Barcol impressor according to ASTM D 2583-93.
UV Cut (nm) is the wavelength for which there is 0.5% or 1.0% transmission.

E', Tg and Max tg (δ) measurement, δ being the loss angle, is done using DMA (dynamic mechanical analysis). Such analysis can be performed on a planar 5.2×1×2 cm (thickness) sample, in a point 3 bending with a Rheometrics Solid Analyzer RSA II apparatus, at a 1 Hz frequency and in a temperature range of −50° C. to 170° C. at 2° C./minute.

Max tg (δ) corresponds to the temperature for the ratio maximum: E" (loss modulus)/E' (conservation modulus).

The refractive index $n_e$ (λ=546 nm), $n_d$ (λ=589 nm) and the Abbe numbers $v_e$, $v_d$ are determined at 25° C.

CONCLUSION

The incorporation of TTPPS in compositions 2 and 3 resulted in an increase of the UV cut, as well as Tg, Max tg(δ), E' at 100° C. and refractive index.

Example 7

Preparation of a Polymer from a Polymerizable Composition According to the Invention BTPPS (0.45 g, 0.0025 moles) was dissolved in dimethylformamide (2 ml) at 80° C. The solution was cooled and MonX (0.216 g, 0.002 moles) was added and stirred at 50° C. for 3.5 hours. Polymer molecular weight was determined using Gel permeation chromatography using polystyrene standards. Polymer had a molecular weight of 4000.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A process for making a thiophosphine compound of formula (I):

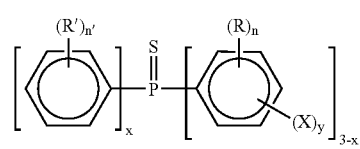

(I)

wherein X represents SH or

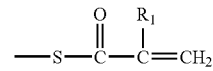

with $R_1$ being H or —$CH_3$, R and R' represent, independently from each other, an alkyl radical, an alkoxy radical, an aryl radical or a phenyl radical which may be substituted with one or more alkyl and/or alkoxy groups, n is an integer from 0 to 4, n' an integer from 0 to 5, x is an integer from 0 to 2, y is an integer from 1 to 5 with the proviso that y+n is an integer from 1 to 5, wherein y=1, X is in para position with regard to phosphorus and represents —SH, the process comprising:

a) reacting in the presence of a catalyst a component A of formula:

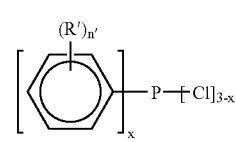

(A)

in which R', n' and x are defined above with a component B of formula:

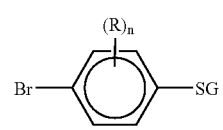

(B)

in which R and n are defined above and G is a blocking radical of the SH function, the molar ratio of components A to B being:

1/3 when x=0
1/2 when x=1, and
1/1 when x=2;

b) isolating from step a) a first intermediate compound C of formula:

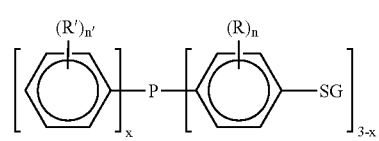

(C)

in which R', n', R, n, and x are defined above;

c) reacting compound C with elemental sulphur;

d) isolating from step c) an intermediate compound D of formula:

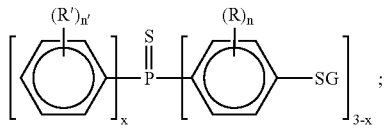

in which R', n', R, n, and x are defined above;

e) reacting intermediate compound D with an alkaline thiolate in a solvent under reflux; and f) isolating from step e) a thiophosphine monomer of formula (I).

2. The process of claim 1, wherein n=n'=0.

3. The process of claim 1, wherein G is $CH_3$.

4. The process of claim 1, wherein the thiolate is sodium 2-methyl-2-propane thiolate.

5. The process of claim 1, wherein the catalyst of step a) is n-butyl lithium.

* * * * *

UNITED STATES PATENT AND TRADEMARK OFFICE
CERTIFICATE OF CORRECTION

| | |
|---|---|
| PATENT NO. | : 7,378,556 B2 |
| APPLICATION NO. | : 11/551439 |
| DATED | : May 27, 2008 |
| INVENTOR(S) | : Sirisoma Wanigatunga et al. |

Page 1 of 1

It is certified that error appears in the above-identified patent and that said Letters Patent is hereby corrected as shown below:

In claim 1, column 20, line 21, please delete "n' an" and insert --n' is an-- therefor.

Signed and Sealed this

Twenty-ninth Day of July, 2008

JON W. DUDAS
*Director of the United States Patent and Trademark Office*